(12) United States Patent
Yamanaka et al.

(10) Patent No.: US 10,436,757 B2
(45) Date of Patent: Oct. 8, 2019

(54) ELECTRICAL SIGNAL PROCESSING DEVICE

(71) Applicant: TOHOKU UNIVERSITY, Sendai-shi, Miyagi (JP)

(72) Inventors: Kazushi Yamanaka, Sendai (JP); Toshihiro Tsuji, Sendai (JP); Toru Oizumi, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 293 days.

(21) Appl. No.: 15/515,886

(22) PCT Filed: Nov. 26, 2015

(86) PCT No.: PCT/JP2015/083290
§ 371 (c)(1),
(2) Date: Mar. 30, 2017

(87) PCT Pub. No.: WO2016/084917
PCT Pub. Date: Jun. 2, 2016

(65) Prior Publication Data
US 2017/0307567 A1     Oct. 26, 2017

(30) Foreign Application Priority Data

Nov. 28, 2014 (JP) ................................ 2014-241817

(51) Int. Cl.
*G01N 29/44*         (2006.01)
*G01N 29/02*         (2006.01)
(Continued)

(52) U.S. Cl.
CPC ............ *G01N 29/44* (2013.01); *G01N 29/02* (2013.01); *G01N 29/022* (2013.01); *G01N 29/24* (2013.01);
(Continued)

(58) Field of Classification Search
CPC ...... G01N 29/02; G01N 29/022; G01N 29/24; G01N 29/2437; G01N 29/348;
(Continued)

(56) References Cited

U.S. PATENT DOCUMENTS 6,005,506 A      12/1999   Bazarjani et al.
8,340,218 B2 *   12/2012   Drennen, III ........ H04B 1/0003
                                                            375/316

(Continued)

FOREIGN PATENT DOCUMENTS

EP      1 577 667 A2     9/2005
EP      1 739 420 A1     3/2007
(Continued)

OTHER PUBLICATIONS

"Chemical and Biological Sensors," Acoustic Wave Sensors, 1997, pp. 222-225.

(Continued)

*Primary Examiner* — David B Lugo
(74) *Attorney, Agent, or Firm* — Oliff PLC

(57) ABSTRACT

When frequencies used in the two-frequency measurement of a SAW sensor are represented by $f_1$ and $f_2$ ($f_2 > f_1$), an electrical signal processing device is provided without use of oversampling at a frequency higher than twice the frequency $f_2$ or a two-system low-frequency conversion circuit, in which temperature compensation with the same accuracy as the case where these are used can be realized. Narrow band frequency filtering is applied to a waveform after roundtrips in a delay line type SAW sensor capable of transmitting and receiving multiple frequencies, the two frequencies $f_1$ and $f_2$ ($f_2 > f_1$) are extracted, and a delay time is determined utilizing an aliasing obtained by applying undersampling at a frequency lower than twice the frequency $f_1$.

9 Claims, 8 Drawing Sheets

(51) Int. Cl.
*G01N 29/24* (2006.01)
*G01N 29/42* (2006.01)
*H01L 41/04* (2006.01)
*H01L 41/113* (2006.01)
*G01N 29/34* (2006.01)
*G01N 29/36* (2006.01)

(52) U.S. Cl.
CPC ....... *G01N 29/2437* (2013.01); *G01N 29/348* (2013.01); *G01N 29/36* (2013.01); *G01N 29/42* (2013.01); *G01N 29/4454* (2013.01); *H01L 41/04* (2013.01); *H01L 41/113* (2013.01); *G01N 2291/0423* (2013.01)

(58) Field of Classification Search
CPC ........ G01N 29/36; G01N 29/42; G01N 29/44; G01N 29/4454; H01L 41/04; H01L 41/113
See application file for complete search history.

(56) References Cited

U.S. PATENT DOCUMENTS

| | | | |
|---|---|---|---|
| 2007/0248180 A1* | 10/2007 | Bowman | G01V 15/00 375/272 |
| 2017/0116442 A1* | 4/2017 | Hines | G01R 15/181 |
| 2017/0299449 A1* | 10/2017 | Nakamura | G01B 17/04 |

FOREIGN PATENT DOCUMENTS

| | | |
|---|---|---|
| JP | S59-147258 A | 8/1984 |
| JP | H11-142425 A | 5/1999 |
| JP | 2005-094610 A | 4/2005 |
| JP | 2005-191650 A | 7/2005 |
| JP | 2005-291955 A | 10/2005 |
| JP | 2005-333457 A | 12/2005 |
| JP | 2006-071482 A | 3/2006 |
| JP | 2007-225509 A | 9/2007 |
| JP | 2008-245003 A | 10/2008 |
| JP | 2015-087271 A | 5/2015 |

OTHER PUBLICATIONS

Inoue, Hirotsugu et al., "Time-Frequency Analysis of Dispersive Stress Waves by Means of Wavelet Transform (Identification of Group Velocity and Application to Ultrasonic Materials Evaluation)," The Japan Society of Mechanical Engineers, 1995, pp. 153-160. NII-Electronic Library Service.

Takayanagi, Kosuke et al., "Detection of Trace Water Vapor Using SiOx-Coated Ball Saw Sensor," Materials Transactions, Jun. 25, 2014, pp. 988-993, vol. 55, No. 7, The Japanese Society for Non-Destructive Inspection.

Yamanaka, Kazushi et al., "Ultramultiple Roundtrips of Surface Acoustic Wave on Sphere Realizing Innovation of Gas Sensors," IEEE Transactions on Ultrasonics, Ferroelectrics, and Frequency Control, Apr. 2006, pp. 793-801, vol. 53, No. 4.

Hagihara, Satoshi et al., "Highly sensitive trace moisture ball surface acoustic wave sensor using SiOx film," Japanese Journal of Applied Physics, 2014, pp. 07KD08-1-07KD08-5, vol. 53.

Abe, Takuji et al., "Evaluation of Response Time in Ball Surface-Acoustic-Wave Hydrogen Sensor using Digital Quadrature Detector," Japanese Journal of Applied Physics, 2007, pp. 4726-4728, vol. 46, No. 7B.

Nakatsukasa, Takuya et al., "Temperature Compensation for Ball Surface Acoustic Wave Devices and Sensor Using Frequency Dispersion," Japanese Journal of Applied Physics, 2006, pp. 4500-4504, vol. 45, No. 5B.

Tsuji, Toshihiro et al., "Highly Sensitive Ball Surface Acoustic Wave Hydrogen Sensor with Porous Pd-Alloy Film," Materials Transactions, 2014, pp. 1040-1044, vol. 55, No. 7, The Japanese for Society for Non-Destructive Inspection.

Feb. 16, 2016 International Search Report issued in International Patent Application No. PCT/JP2015/083290.

Oct. 20, 2017 Search Report issued in European Patent Application No. 15863626.6.

Kester, Walt, Section 5, Undersampling Applications (1995).

* cited by examiner

ELECTRICAL SIGNAL PROCESSING DEVICE

TECHNICAL FIELD

The present invention relates to a simplified electrical signal processing device for spreading the use of a highly sensitive trace moisture sensor, a hydrogen gas sensor, and a volatile-organic-compounds sensor using a surface acoustic wave (SAW) device and their application to a portable gas chromatograph and a wearable environment measuring instrument.

BACKGROUND ART

Conventionally, by use of a sensitive film which is formed on the propagation path of the SAW device and a SAW sensor which measures an acoustic velocity variation caused by reaction of the sensitive film with gas molecules, highly sensitive gas sensors have been developed (see, for example, non-patent literature 1). Although the sensitivity of the sensor can be enhanced by increasing the interaction length of the SAW with the sensitive film, there is a limitation on an available interaction length due to diffraction caused by propagation.

On the other hand, it is possible to propagate a diffraction-free SAW which is naturally collimated on a spherical surface, when the aperture of the sound source of the SAW is selected to be the geometric mean of the diameter of a sphere and the wavelength of SAW, where the effect of diffraction caused by the propagation is balanced with that of focusing caused by the spherical surface (see, for example, patent literatures 1 and 2 and non-patent literature 2). A ball SAW sensor is the sensor utilizing this phenomenon which brings multiple roundtrips of the SAW on an equator with respect to the Z-axis cylinder of a piezoelectric crystal sphere and thus the interaction length of the ball SAW sensor is significantly increased compared with that in a planar SAW sensor (see, for example, non-patent literature 2). Since a variation in the delay time of the SAW caused by a variation in the velocity of the sensitive film is amplified in proportion to the number of the roundtrips, it is possible to perform a highly precise measurement of the delay time, resulting in realizing a highly sensitive gas sensor (see, for example, patent literatures 3 and 4 and non-patent literatures 2, 3, 4 and 5).

However, in order to effectively utilize this principle, it is necessary to perform temperature compensation with high precision, which remove a variation in the delay time caused by a variation in the velocity owing to a variation in the temperature of a device. Although a substrate with a crystal orientation of small temperature coefficient of the velocity can be used in the planar SAW sensor, such a substrate cannot be used in the ball SAW sensor because a crystal orientation is continuously changed along the propagation path. Although the temperature compensation can be realized by obtaining a difference between the outputs of equivalent devices with and without a sensitive film, it is not easy to make the temperature of the propagation path in one device identical to that in the other installed at separate location.

Here, since the temperature coefficient of relative velocity change of the piezoelectric crystal can be represented by a constant value independent of a frequency, for example, ppm/° C., relative delay time change is also independent of the frequency. On the other hand, since the relative delay time change caused by a variation in the velocity owing to reaction of the sensitive film with the gas molecules is proportional to the frequency, precise temperature compensation is realized by a difference of the relative delay time changes at two different frequencies on identical propagation path, typically represented by a unit of ppm, which is named as two-frequency measurement (TFM). A sensor capable of generating two frequencies is developed by use of a ball SAW sensor that can transmit and receive odd-order harmonics using a double interdigital electrode (see, for example, patent literatures 5 and 6 and non-patent literature 6).

In order to realize the measurement of the delay time change with sufficient precision for TFM, for example, it is necessary to use an analog-to-digital converter (ADC) with a sampling rate twice higher than the third harmonic frequency so as to record a waveform in the case of oversampling and to thereafter perform processing with a high time resolution such as a wavelet analysis (see, for example, non-patent literature 8). On the other hand, it is possible to measure the phase of the received signal using an ADC with low sampling rate, when the frequency of a received signal is reduced by heterodyne detection. (see, for example, patent literature 7 and non-patent literature 7).

CITATION LIST

Patent Literature

Patent Literature 1: Japanese Unexamined Patent Application Publication No. 2005-94610
Patent Literature 2: Japanese Unexamined Patent Application Publication No. 2005-191650
Patent Literature 3: Japanese Unexamined Patent Application Publication No. 2005-291955
Patent Literature 4: Japanese Unexamined Patent Application Publication No. 2007-225509
Patent Literature 5: Japanese Unexamined Patent Application Publication No. 2006-71482
Patent Literature 6: Japanese Unexamined Patent Application Publication No. 2008-245003
Patent Literature 7: Japanese Unexamined Patent Application Publication No. 2005-333457

Non Patent Literature

Non Patent Literature 1: D. S. Ballantine, R. M. White, S. J. Martin, A. J. Ricco, E. T. Zellers, G. C. Frye, and H. Wohltjen, "Acoustic Wave Sensors Theory, Design, and Physico-Chemical Applications", Academic Press 1996
Non Patent Literature 2: K. Yamanaka, S. Ishikawa, N. Nakaso, N. Takeda, D-Y. Sim, T. Mihara, A. Mizukami, I. Satoh, S. Akao, and Y. Tsukahara, "Ultramultiple Roundtrips of Surface Acoustic Wave on Sphere Realizing Innovation of Gas Sensors", IEEE Trans. UFFC., 2006, 53, p. 793-801
Non Patent Literature 3: K. Takayanagi, S. Akao, T. Yanagisawa, N. Nakaso, Y. Tsukahara, S. Hagihara, T. Oizumi, N. Takeda, T. Tsuji, and K. Yamanaka, "Detection of Trance Water Vapor Using SiOx-Coated Ball SAW Sensor", Mater. Trans., 2013, 55, p. 988-993
Non Patent Literature 4: S. Hagihara, T. Tsuji, T. Oizumi, N. Takeda, S. Akao, T. Ohgi, K. Takayaangi, T. Yangisawa, N. Nakaso, Y. Tsukahara, and K. Yamanaka, "Highly sensitive trace moisture ball surface acoustic wave sensor using SiOx film", Jpn. J. Appl. Phys., 2014, 53, 07KD08
Non Patent Literature 5: T. Tsuji, R. Mihara, T. Saito, S. Hagihara, T. Oizumi, N. Takeda, T. Ohgi, T. Yanagisawa, S. Akao, N. Nakaso, and K. Yamanaka, "Highly Sensitive Ball Surface Acoustic Wave Hydrogen Sensor with Porous Pd-Alloy Film", Mater. Trans., 2013, 55, p. 1040-1044

Non Patent Literature 6: T. Nakatsukasa, S. Akao, T. Ohgi, N. Nakaso, T. Abe, and K. Yamanaka, "Temperature Compensation for Ball Surface Acoustic Wave Devices and Sensor Using Frequency Dispersion", Jpn. J. Appl. Phys., 2006, 45(5B), p. 4500-4054

Non Patent Literature 7: T. Abe, N. Iwata, T. Tsuji, T. Mihara, S. Akao, K. Noguchi, N. Nakaso, D-Y. Sim, Y. Ebi, T. Fukiura, H. Tanaka, and K. Yamanaka, "Evaluation of Response Time in Ball Surface-Acoustic-Wave Hydrogen Sensor using Digital Quadrature Detector", Jpn. J. Appl. Phys., 2007, 46, p. 4726

Non Patent Literature 8: Hiroshi Inoue, Kikuo Kishimoto, Tomoaki Nakanishi, Hisaichi Shibuya, "Time-Frequency Analysis of Dispersive Stress Waves by Wavelet Transform", Technical Journal of the Japan Society of Mechanical Engineers, 1995, 61, p. 153

SUMMARY OF INVENTION

Technical Problem

Disadvantageously, however, since the performance of an ADC needed in a ball SAW sensor as disclosed in non-patent literature 2, 3, 4, and 6 is equivalent to that of the ADC installed in a highly accurate digital oscilloscope, such a ADC is expensive. Although an inexpensive ADC with low sampling rate can be used according to measurement methods as disclosed in patent literature 7 and non-patent literatures 5 and 7, the two systems of heterodyne detection, composed of four oscillators and two nonlinear circuit elements, are needed in the TFM, resulting in the circuit disadvantageously expensive. Moreover, the instability of the nonlinear circuit element may disadvantageously cause a drift in the phase output of a sensor in a long-term measurement such as a measurement for one year.

The present invention is made in view of the foregoing problems and has an object to provide an inexpensive electrical signal processing device which can realize highly precise temperature compensation in a SAW sensor using the TFM.

Solution to Problem

In general, when a received signal is undersampled, a low-frequency aliasing output is produced (see, for example, S. M. Kuo, B. H. Lee, "Real-time Digital Signal Processing", John Wiley&Sons, Ltd., 2001, New York, p. 154). Here, the frequency of the aliasing (hereinafter referred to as the "aliasing frequency") is given as follows:

$$f_{image}(N)=|f-Nf_S| \quad (1)$$

where f represents the frequency of the received signal, fs represents a sampling frequency, and N represents an integer.

The present inventors et al. have attempted to apply undersampling to the TFM in a ball SAW sensor without use of an expensive ADC nor a two-system low-frequency conversion circuit in order to reduce the production cost of a measurement system. Since they have found that highly precise temperature compensation can be realized using undersampling contrarily to expectations, they have conceived the present invention. This type of technology has not yet been proposed.

Specifically, an electrical signal processing device according to the present invention, with respect to two frequencies $f_1$ and $f_2$ with a relationship of $f_2=3f_1$, the electrical signal processing device includes an ADC (analog-to-digital converter) which samples a signal from a delay line type SAW (surface acoustic wave) sensor that can transmit the two frequencies $f_1$ and $f_2$ and receive two frequencies one of which is equal to or more than $f_1$ (1−¹⁄₁₀) but equal to or less than $f_1$ (1+¹⁄₁₀) and the other of which is equal to or more than $f_2$ (1−¹⁄₁₀) but equal to or less than $f_2$ (1+¹⁄₁₀), a sampling frequency $f_S$ of the ADC is $f_S=5f_1/4$ and, among signals sampled by the ADC, signals of two frequencies $f_{u1}=f_1/4$ and $f_{u2}=f_1/2$ are used for measurement of a response.

In the electrical signal processing device according to the present invention, the ADC may be synchronized with a transmitted signal to the SAW sensor. The electrical signal processing device according to present invention may include band-pass filters (BPFs) whose center frequencies are $f_1$ and $f_2$ and whose band widths are equal to or less than 20% of the center frequencies so as to process a received signal from the SAW sensor and to extract components of $f_1$ and $f_2$, and the ADC may be configured so as to sample a signal extracted by the BPFs. The BPFs may be formed with BPF for extracting the component of $f_1$ and BPF for extracting the component of $f_2$, and the ADCs may also be formed with two ADCs so as to correspond to these BPFs.

The electrical signal processing device according to the present invention may include a digital filter which can interrupt aliasing frequencies other than the two frequencies $f_{u1}$ and $f_{u2}$ from the signal sampled by the ADC. The digital filters may be formed with two digital filters one of which interrupts the aliasing of frequencies other than $f_{u1}$ and the other of which interrupts the aliasing of frequencies other than $f_{u2}$.

The SAW sensor may be a delay line type SAW sensor on a planar substrate, and the SAW sensor may be a ball SAW sensor.

In the electrical signal processing device according to the present invention, since narrow BPFs are applied to a waveform received from the SAW sensor capable of transmitting and receiving multiple frequencies, the two frequencies $f_1$ and $f_2$ ($f_2>f_1$) are extracted. Aliasing waveforms caused by undersampling lower than twice the frequency $f_1$ are used for determining delay times relevant to two frequencies $f_1$ and $f_2$. With the result that it is possible to most effectively solve the problems described above.

Advantageous Effects of Invention

According to the present invention, it is possible to provide an electrical signal processing device in which temperature compensation can be realized using undersampling with the same precision as the case that oversampling higher than twice the frequency $f_2$ or a two-system low-frequency conversion circuit, where frequencies used in the TFM of the SAW sensor are represented by $f_1$ and $f_2$ ($f_2>f_1$). Hence, according to the present invention, it is possible to simplify the TFM system which can perform practical temperature compensation on the ball SAW sensor and provide it inexpensively.

DESCRIPTION OF EMBODIMENTS

An embodiment of the present invention will be described below with reference to drawings.

As the first example, it is indicated that undersampling performed with a simplified electrical signal processing device is useful for temperature compensation performed in a TFM using a sensor in which a sol-gel SiOx film for measurement of trace moisture is formed on a harmonic ball SAW device. Here, it is indicated that it is possible to clearly measure a response to trace moisture of 20 nmol/mol which is conventionally difficult to measure without use of a CRDS (cavity ring-down spectroscopy), and that temperature-compensated sensor response with undersampling agrees with that with oversampling with a correlation coefficient of 0.9999.

Figure 1:
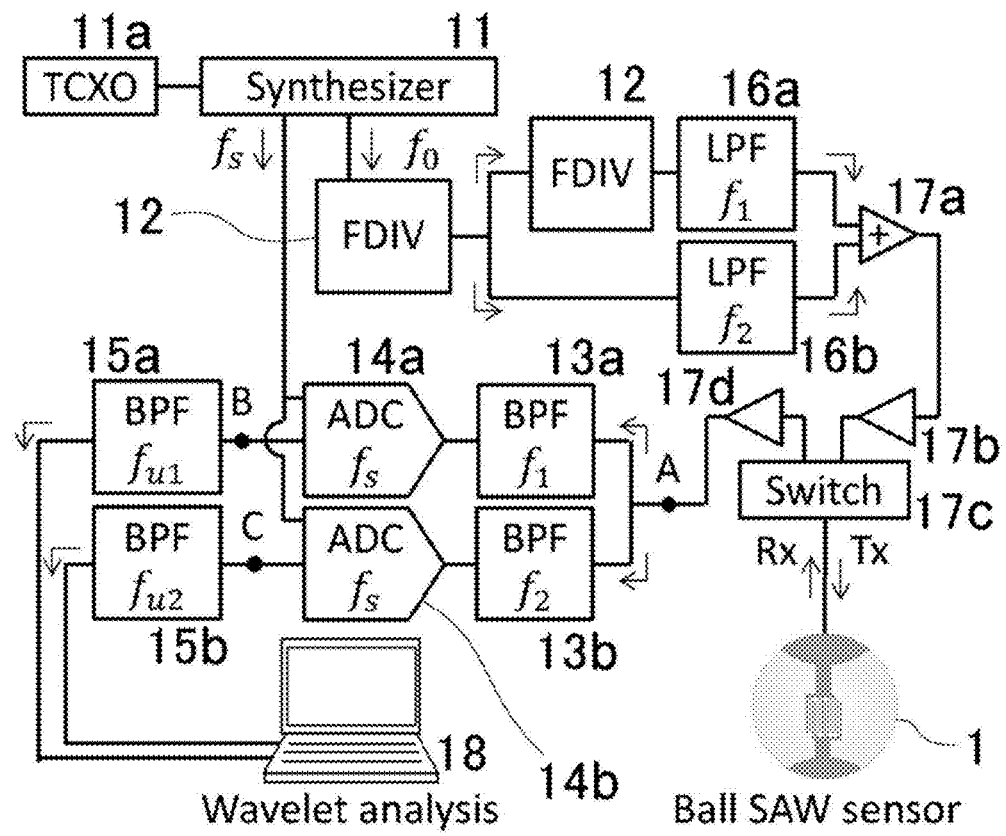
FIG. 1 a block diagram showing the first example in a TFM system which shows a concept of an electrical signal processing device according to an embodiment of the present invention.

FIG. 1 shows a block diagram of a TFM system. Here, $f_S$ is the sampling frequency of an ADC, $f_1$ and $f_2$ ($f_2 > f_1$) are two frequencies which are transmitted and received by a delay line type SAW sensor and $f_0$ represents a frequency which is a common multiple of $f_1$ and $f_2$. Furthermore, $f_{u1}$ and $f_{u2}$ represent two aliasing frequencies utilized for measurement of a response among outputs obtained by undersampling, which are respectively caused by $f_1$ and $f_2$.

First, with a synthesizer 11 which utilizes a temperature-compensated crystal oscillator (TCXO) 11a as the reference oscillator, the continuous signal of $f_0$ synchronized with $f_S$ is generated. The signal of $f_0$ is divided in frequency with a frequency divider (FDIV) 12 so as to be converted into the signals of $f_1$ and $f_2$, and the signals of $f_1$ and $f_2$ are respectively processed with low-pass filters (LPF) 16a and 16b and are thereafter combined with an adder 17a such that a transmitted signal Tx is generated. The transmitted signal Tx is amplified by an amplifier 17b, is passed through a rf switch 17c and is input to a SAW sensor 1. A reflected signal Rx from the SAW sensor 1 is passed through the rf switch 17c, is amplified by an amplifier 17d, is thereafter processed with narrow band-pass filters (BPF) 13a and 13b whose center frequencies are $f_1$ and $f_2$ and are recorded in ADCs 14a and 14b. Among the signals recorded in the ADCs 14a and 14b, signals whose frequency components are not $f_{u1}$ and $f_{u2}$ are interrupted with BPFs 15a and 15b, and a delay time is measured with a computer 18.

In the present example, a case where the SAW sensor 1 is a ball SAW sensor, $f_S = 5f_1/4$, $f_2 = 3f_1$, $f_{u1} = |f_1 - f_S| = f_1/4$ and $f_{u2} = |3f_1 - 2f_S| = f_1/2$ will be described. For the measurement of the delay time, a wavelet analysis was utilized.

In a verification experiment, first, a sol-gel SiOx film for measurement of trace moisture was formed on a harmonic ball SAW device (made of quartz with a diameter of 3.3 mm, $f_1 = 80$ MHz) and thus a sensor was produced, and a roundtrip waveform was measured with a broadband pulsar receiver and was recorded using a digital oscilloscope with averaging processing of 1024 times by oversampling (5 GHz).

Then, BPFs whose center frequencies were $f_1$ and $f_2$ and whose band widths were 5% of the individual frequencies were applied to this waveform by FFT and thereafter the waveform was sampled with a sampling frequency $f_S$ in order to simulate the situation in which $f_S$ was synchronized with a transmitted signal.

Then, in order to measure the delay time, a wavelet transform was performed where a Gabor function ($\gamma = 50$) was used as a mother wavelet. Here, the wavelet transform was performed at $f_1$ and $f_2$ in the case of oversampling whereas it was performed at $f_{u1}$ and $f_{u2}$ in the case of undersampling. The delay time was measured from a propagation time difference between the roundtrip waves of the third turn and the seventh turn.

Figure 2:
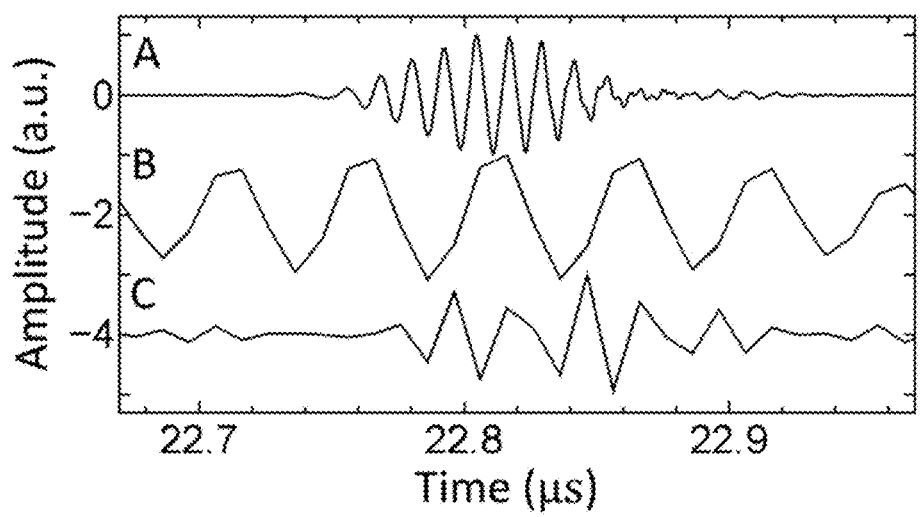
FIG. 2 is a graph showing waveforms measured at positions A to C in FIG. 1.

In A of FIG. 2, the waveform obtained by performing oversampling at position A in FIG. 1 is indicated. On the other hand, in B and C of FIG. 2, the waveforms (waveforms at positions B and C in FIG. 1) obtained by performing undersampling after the application of the BPFs are indicated.

Figure 3:
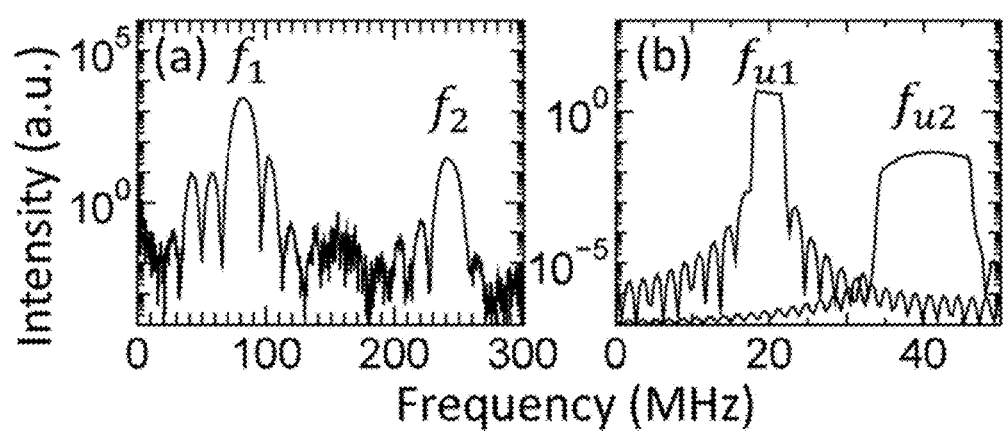
FIG. 3(a) is a power spectrum of the waveform A in FIG. 2.
FIG. 3(b) is those of the waveforms B and C in FIG. 2.

FIG. 3 shows power spectra corresponding to the waveforms of FIG. 2. As shown in FIG. 3(a), the components of $f_1$ and $f_2$ were confirmed in the spectrum of the waveform obtained by performing oversampling and, as shown in FIG. 3(b), the components of $f_{u1}$ and $f_{u2}$ were confirmed in the spectrum of the waveform obtained by performing undersampling.

Figure 4:
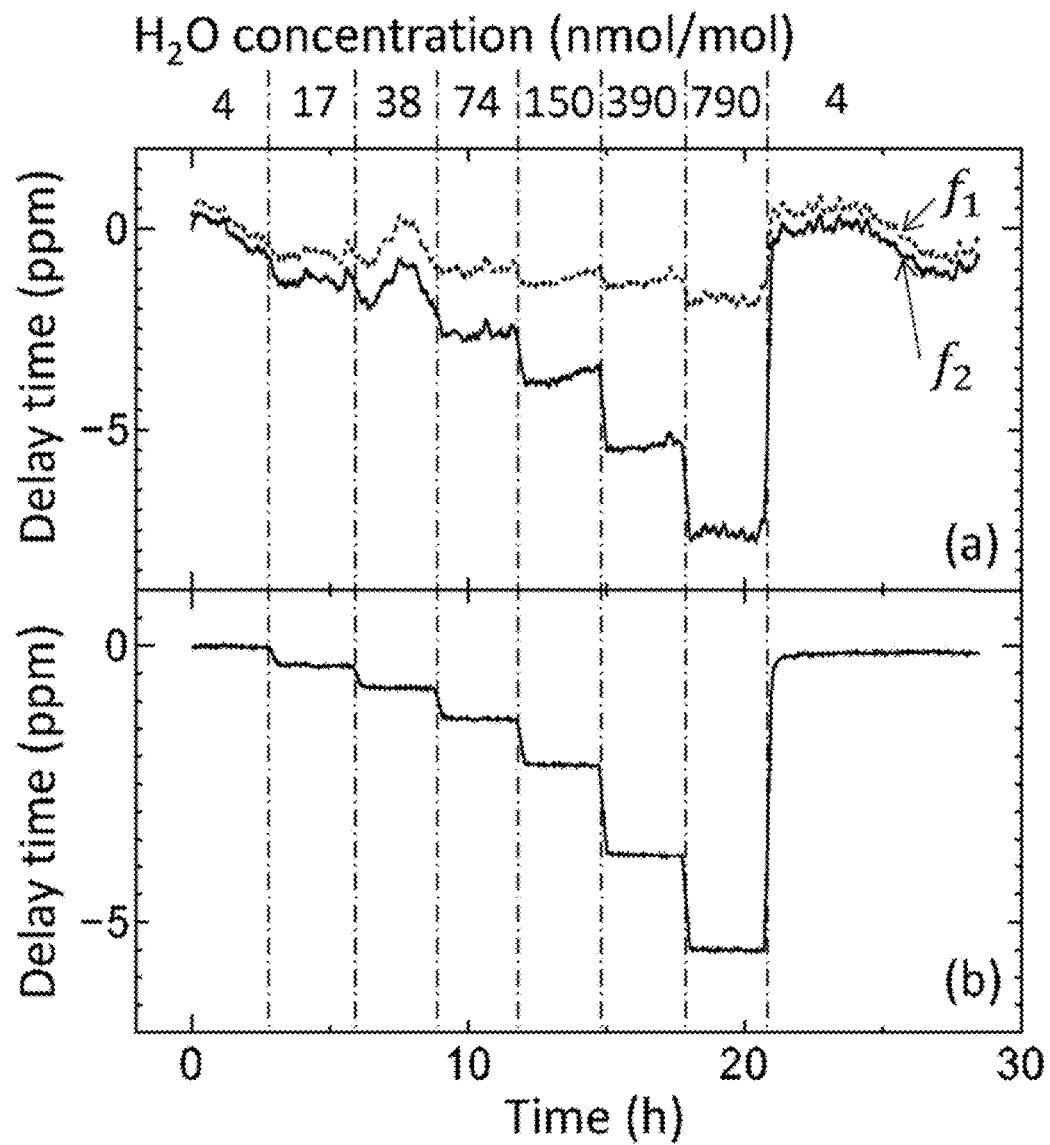
FIG. 4(a) is a graph showing relative delay time changes in a TFM performed from oversampled waveforms, where a sequence of trace moisture variation is measured.
FIG. 4(b) is a graph showing the relative delay time change when temperature compensation is further performed.

FIG. 4 shows results of a TFM on $f_1$ and $f_2$ performed from the waveform obtained by oversampling, when moisture concentration ($H_2O$ concentration) was generated by step sequence from 4 to 790 nmol/mol with a trace moisture generator. In FIG. 4(a), a broken curve and a solid curve respectively indicate relative delay time changes at $f_1$ and $f_2$. FIG. 4(b) is a result showing a difference between the output of $f_2$ and the output of $f_1$ with a coefficient of 1.0. A moisture response became clear by the temperature compensation, and thus a response to 4 to 17 nmol/mol was measured with a signal-to-noise ratio S/N=44.8.

Figure 5:
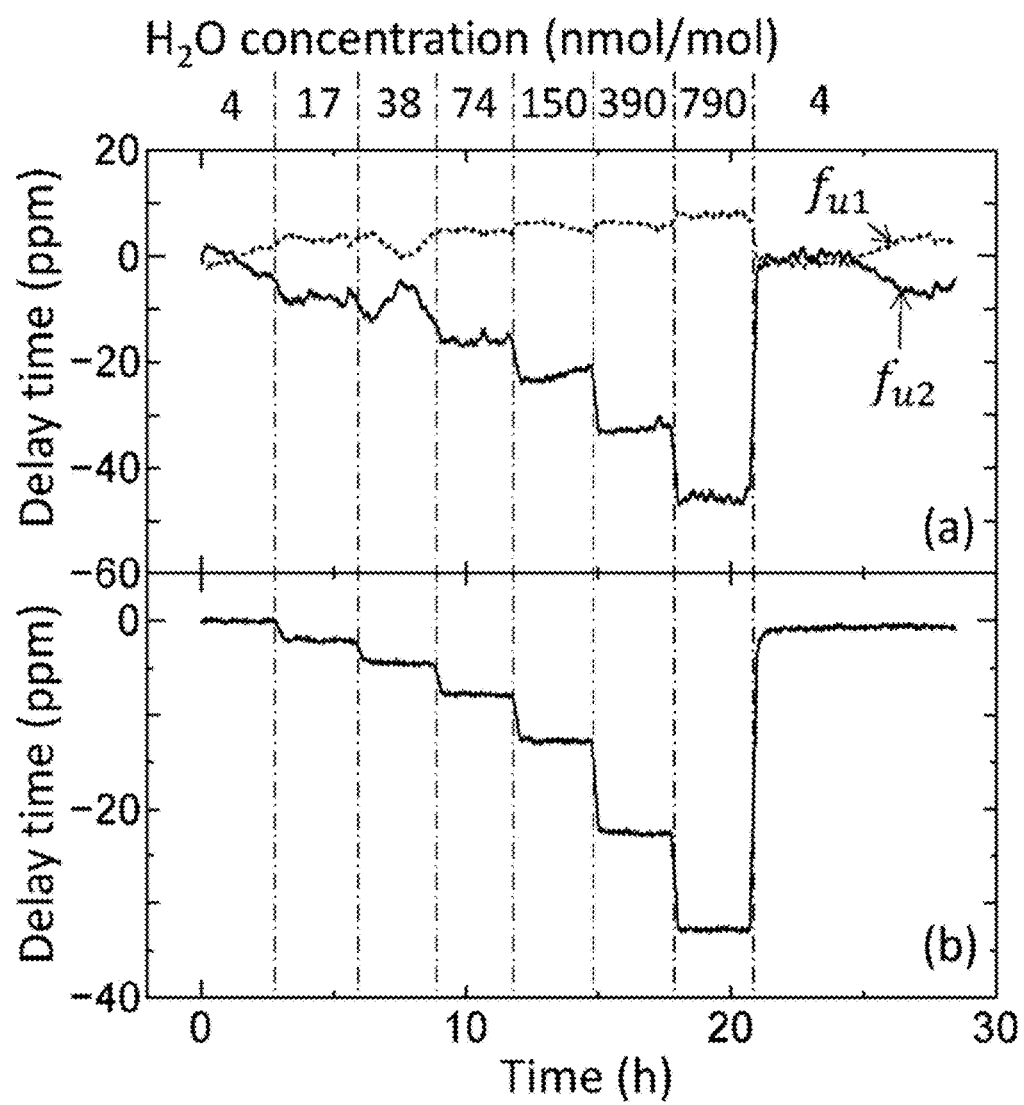
FIG. 5(a) is a graph showing relative delay time changes in a TFM performed from undersampled waveforms, where a sequence of trace moisture variation is measured with the TFM system shown in FIG. 1.
FIG. 5(b) is a graph showing the relative delay time change when temperature compensation is further performed.

As in the case of FIG. 4, FIG. 5 shows results obtained when undersampling was simulated. In FIG. 5(a), a broken curve and a solid curve respectively represent the outputs of $f_{u1}$ and $f_{u2}$. A difference between the output of $f_{u2}$ and the output of $f_{u1}$ was obtained with a coefficient of −1.5 taking the enlargement rate of the output of undersampling into account as shown in FIG. 5(b), where the same temperature compensation as shown in FIG. 4(b) was achieved. This response agreed with the response in oversampling by a linear function with a correlation coefficient of |R|=0.9999.

Although in the first example, the oversampling and the simulated undersampling within the computer were used, an electrical signal processing device was applied to a trace moisture sensor formed with a ball SAW sensor as the second example, where oversampling is not used, that is, a burst waveform is transmitted and received signal was processed with narrow BPFs, and undersampling was applied to BPF-processed waveforms. Specifically, a ball SAW sensor with a diameter of 3.3 mm in which an amorphous silica film synthesized by a sol-gel method was used as a sensitive film was installed in an ultra-high vacuum cell, and the flow of $N_2$ gas (1 L/min) generated using a trace moisture generator utilizing a diffusion tube method was measured.

Figure 6:
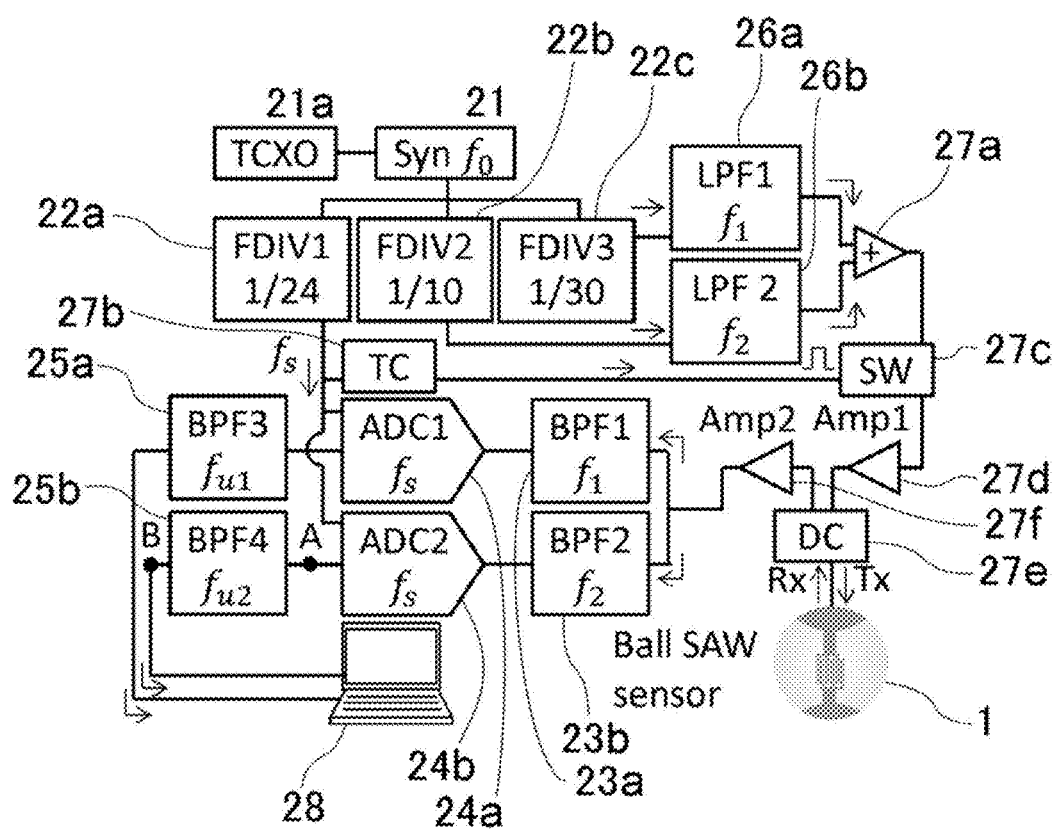
FIG. 6 a block diagram showing the second example in the TFM system which includes the electrical signal processing device according to the embodiment of the present invention.

A block diagram of a TFM system here is shown in FIG. 6. Here, $f_S$ is the sampling frequency of an ADC, $f_1$ and $f_2$ ($f_2 > f_1$) are two frequencies which are transmitted and received by a delay line type SAW sensor and $f_0$ represents a frequency which is a common multiple of $f_1$ and $f_2$. Furthermore, $f_{u1}$ and $f_{u2}$ represent two aliasing frequencies which are utilized for measurement of a response among outputs obtained by undersampling, and they are respectively caused by $f_1$ and $f_2$.

In the measurement, first, an output ($f_0$=2.4 GHz) of a synthesizer (Syn) 21 utilizing a temperature-compensated crystal oscillator (TCXO) 21a as the reference oscillator is divided in frequency with frequency dividers (FDIV1,2,3) 22a, 22b and 22c so as to respectively generate the signals of $f_S$=100 MHz, $f_2$=240 MHz and $f_1$=80 MHz. The signals of $f_1$ and $f_2$ are processed with low-pass filters (LPF1,2) 26a and 26b and are thereafter combined with an adder 27a. A switch signal of a timing controller (TC) 27b synchronized with the signal of $f_S$ is used for controlling an rf switch (SW) 27c for generating a transmitted burst signal Tx. The transmitted burst signal Tx is amplified by an amplifier (Amp1) 27d, is passed through a directional coupler (DC) 27e, and is input to the SAW sensor 1. A reflected signal Rx from the SAW sensor 1 is passed through the directional coupler 27e, is amplified by an amplifier (Amp2) 27f, is thereafter processed with narrow band-pass filters (BPF) 23a and 23b whose Q values are respectively 20 and 40 and whose center frequencies are respectively $f_1$ and $f_2$, and is recorded in ADCs 24a and 24b. The input of the transmitted burst signal Tx to the SAW sensor 1 and the output of the reflected signal Rx from the SAW sensor 1 are switched with the directional coupler 27e. Among the signals recorded in the ADCs 24a and 24b, signals whose frequency components are not $f_{u1}$ and $f_{u2}$ are interrupted with BPFs 25a and 25b, and a delay time is measured with a computer 28. Here, the wavelet transform using a Gabor function ($\gamma$=50) is applied to the BPFs 25a and 25b in order to extract the outputs of undersampling frequencies ($f_{u1}$=20 MHz, $f_{u2}$=40 MHz) which satisfy a sampling theorem.

In the present example, the SAW sensor 1 is a ball SAW sensor, $f_S$=5$f_1$/4, $f_2$=3$f_1$, $f_{u1}$=|$f_1$−$f_S$|=$f_1$/4 and $f_{u2}$=|3$f_1$−2$f_S$|=$f_1$/2. For the measurement of the delay time, the wavelet analysis was utilized.

Figure 7:
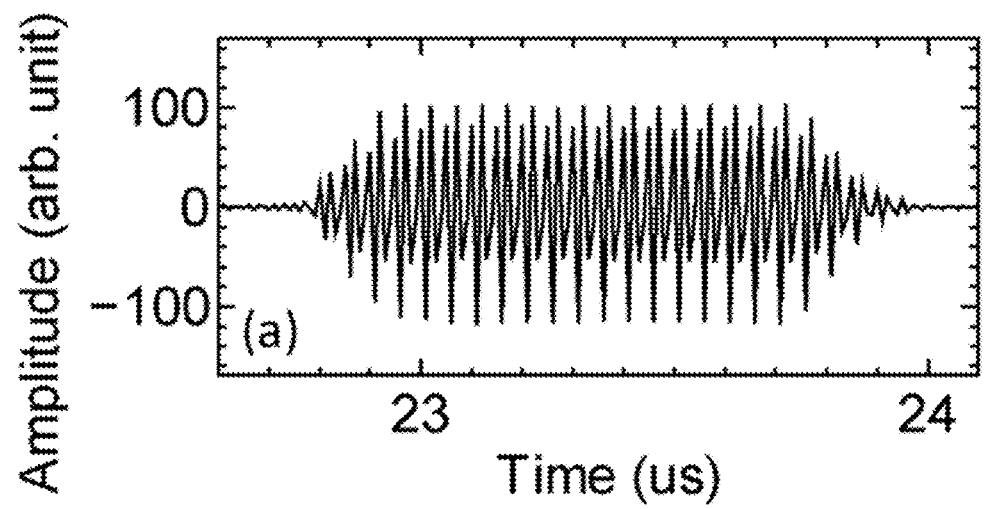
FIG. 7(a) is a graph showing a waveform measured at position A in FIG. 6.
FIG. 7(b) is a graph showing a spectrum (solid curve) obtained by the waveform in FIG. 7(a) processed by FFT and that (broken curve) obtained by the waveform resulting from wavelet transform at position B in FIG. 6 processed by FFT.
Figure 7:
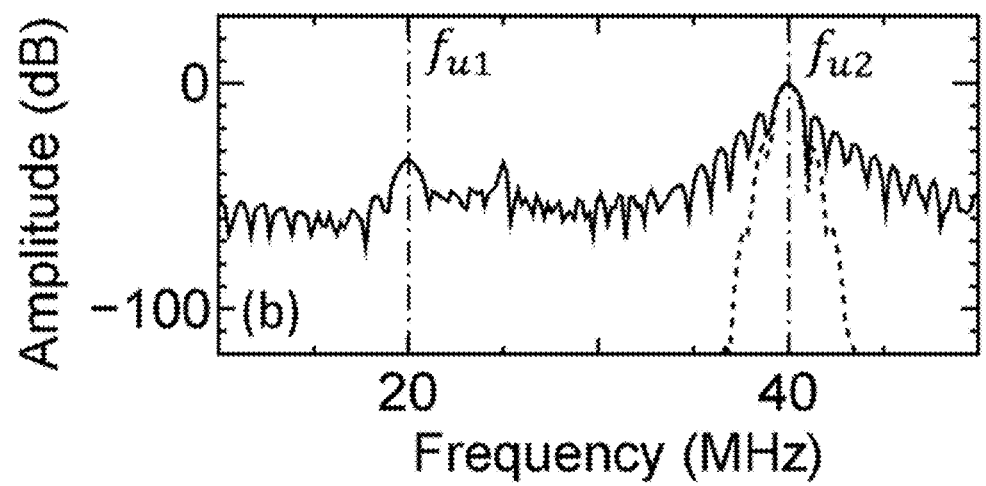

A waveform obtained by performing undersampling at position A in FIG. 6 is shown in FIG. 7(a). A spectrum obtained by performing FFT on the waveform is indicated by a solid curve in FIG. 7(b). The components of $f_{u1}$ and $f_{u2}$ were confirmed in the spectrum of the waveform after undersampling. The amplitude of $f_{u2}$ here was about 33.8 dB larger than that of $f_{u1}$.

Figure 8:
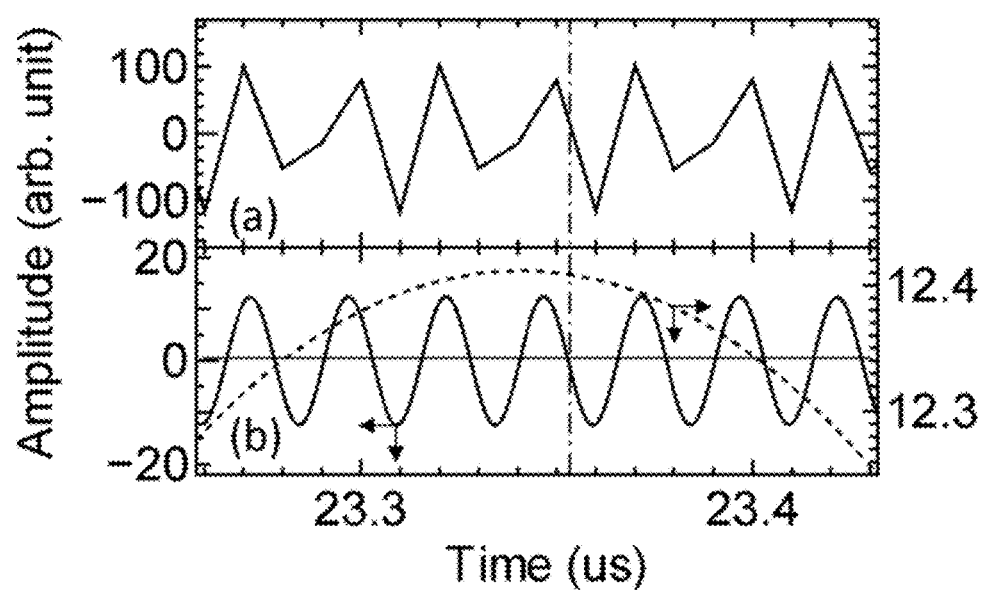
FIG. 8(a) is a graph showing the waveform measured at position A in FIG. 6.
FIG. 8(b) is a graph showing the waveforms resulting from wavelet transform at position B in FIG. 6, where a real part value is indicated by a solid curve and an absolute value is indicated by a broken curve.

A part of the waveform in FIG. 7(a) obtained by performing undersampling at position A in FIG. 6 is shown in FIG. 8(a). A waveform obtained by performing wavelet transform at position B in FIG. 6, that is, a waveform obtained by performing wavelet transform on FIG. 8(a) and then performing 100-point interpolation is shown in FIG. 8(b). A solid curve in FIG. 8(b) indicates a real part value, and a broken curve indicates an absolute value (envelope curve). A zero cross time (position indicated by an alternate long and short dashed line in FIG. 8(b)) closest to the peak of the absolute value was measured as the delay time. A spectrum obtained by performing FFT on the real part waveform of FIG. 8(b) is indicated by a broken curve in FIG. 7(b).

Figure 9:
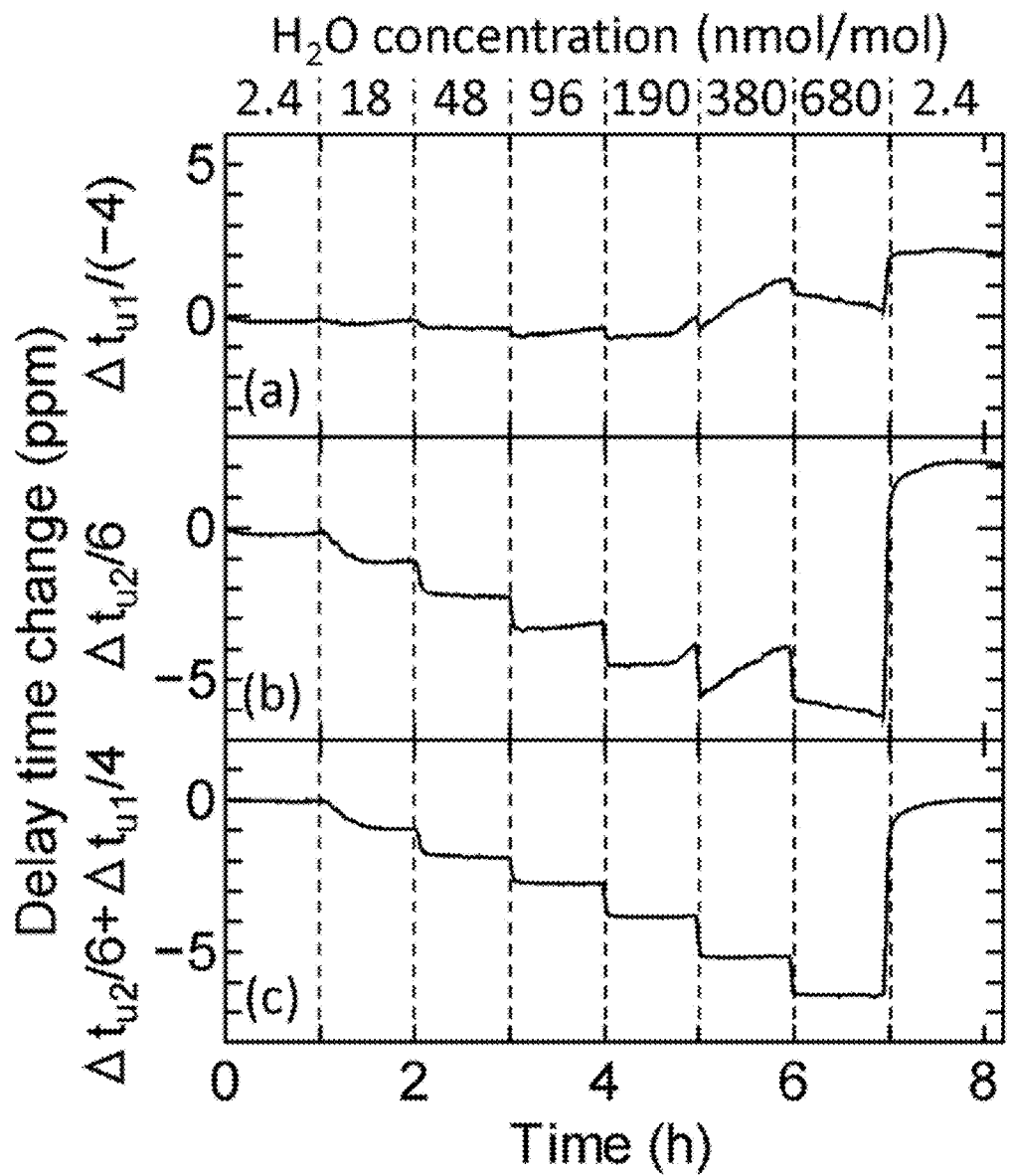
FIG. 9(a) is a graph showing the relative delay time changes in the signal of an aliasing frequency $f_{u1}$ when trace moisture is measured with the TFM system shown in FIG. 6.
FIG. 9(b) is a graph showing the relative delay time change in the signal of an aliasing frequency $f_{u2}$ when trace moisture is measured with the TFM system shown in FIG. 6
FIG. 9(c) is a graph showing the relative delay time change when temperature compensation is performed.

FIGS. 9(a) and 9(b) respectively show relative delay time changes in signals between the third turn and the seventh turn at aliasing frequencies $f_{u1}$ and $f_{u2}$ when the moisture concentration ($H_2O$ concentration) was generated by step sequence from 2.4 to 680 nmol/mol with a trace moisture generator. FIGS. 9(a) and 9(b) respectively show results obtained when relative delay time changes $\Delta t_{u1}$ and $\Delta t_{u2}$ at $f_{u1}$ and $f_{u2}$ were divided by the enlargement rate of the output in undersampling.

FIG. 9(c) shows a result of the temperature compensation which is a difference between the relative delay time change $\Delta t_{u2}$ at $f_{u2}$ and the relative delay time change $\Delta t_{u1}$ at $f_{u1}$. Although in FIGS. 9(a) and 9(b), significant variations in the output were recognized from 4 to 7 hour for the constant moisture concentration as shown in FIG. 9(c), the temperature compensation was performed by obtaining the difference, and thus such variations were able to be removed. A signal-to-noise ratio of a response to 2.4 to 18 nmol/mol was 92.1 because an rms noise was evaluated as 0.00998 ppm in the time range from 0 to 1 hour.

As described above, it was confirmed that in any of the examples, the 100 MHz ADC can be used for the measurement of 240 MHz. Hence, it can be said that according to the present invention, it is possible to simplify the TFM system which can perform practical temperature compensation on the ball SAW sensor and provide it inexpensively.

Although in the examples of the present invention, the case where the ball SAW sensor was used as the delay line type SAW sensor has been described, the present invention can also be applied to a case where a delay line type SAW sensor of a general planar substrate is used and a case where a delay line type SAW sensor using a SAW making round-trips around a substrate is used.

REFERENCE SIGNS LIST

1 SAW sensor
11 synthesizer
11a temperature-compensated crystal oscillator
12 frequency divider
13a, 13b narrow band-pass filter
14a, 14b ADC
15a, 15b band-pass filter
16a, 16b low-pass filter
17a adder
17b, 17d amplifier
17c rf switch
18 computer
21 synthesizer 21a temperature-compensated crystal oscillator
22a, 22b, 22c frequency divider
23a, 23b narrow band-pass filter
24a, 24b ADC
25a, 25b band-pass filter
26a, 26b low-pass filter
27a adder
27b timing controller
27c rf switch
27d, 27f amplifier
27e directional coupler
28 computer

The invention claimed is:

1. A two-frequency measurement (TFM) system comprising:
   a delay line type surface acoustic wave (SAW) sensor, the SAW sensor configured to:
   transmit the two frequencies f1 and f2, where f2=3f1, and
   receive two frequencies, one of which is equal to or more than f1 (1−1/10) but equal to or less than f1 (1+1/10) and the other of which is equal to or more than f2 (1−1/10) but equal to or less than f2 (1+1/10); and
   an electrical signal processing device including an analog-to-digital converter (ADC) configured to sample a signal from the SAW sensor, with a sampling frequency $f_S$ of $f_S=5f_1/4$,
   wherein among signals sampled by the ADC, signals of two frequencies $f_{u1}=f_1/4$ and $f_{u2}=f_1/2$ are used for obtaining a temperature-compensated sensor response by two-frequency measurement.

2. The TFM system according to claim 1,
   wherein a sampling clock of the ADC is synchronized with a transmitted signal to the SAW sensor.

3. The TFM system according to claim 1,
   wherein the electrical signal processing device comprises band-pass filters whose center frequencies are $f_1$ and $f_2$ and whose band widths are equal to or less than 20% of the center frequencies so as to process a received signal from the SAW sensor and to extract components of $f_1$ and $f_2$, and
   wherein the ADC is configured so as to sample a signal extracted by the band-pass filters.

4. The TFM system according to claim 1,
   wherein the electrical signal processing device comprises a digital filter which can interrupt aliasing of a frequency other than the two frequencies $f_{u1}$ and $f_{u2}$ from the signals sampled by the ADC.

5. The TFM system according to claim 1,
   wherein the SAW sensor is a delay line type SAW sensor which uses a SAW that makes roundtrips around a substrate.

6. The TFM system according to claim 1,
   wherein the SAW sensor is a ball SAW sensor.

7. The TFM system according to claim 1,
   wherein relative delay time changes $\Delta t_{u1}$ and $\Delta t_{u2}$ at the two frequencies $f_{u1}$ and $f_{u2}$, respectively, are determined among the signals sampled by the ADC, and a temperature-compensated delay time change is obtained by a calculation formula $\Delta t_{u2}/6+\Delta t_{u1}/4$.

8. The TFM system according to claim 4, further comprising a computer coupled to the digital filter, the computer being programmed to:
   receive signals with the frequencies $f_{u1}$ and $f_{u2}$ from the digital filter, and
   measure a delay time to obtain a temperature-compensated sensor response.

9. The TFM system according to claim 8, wherein the computer is programmed to measure the delay time using a wavelet analysis.

* * * * *